US012662690B2

(12) United States Patent
Zhu et al.

(10) Patent No.: US 12,662,690 B2
(45) Date of Patent: Jun. 23, 2026

(54) CARBONYL REDUCTASE MUTANT, PREPARATION METHOD AND USE THEREOF, AND PREPARATION METHOD OF ETHYL (R)-6-HYDROXY-8-CHLOROOCTANOATE

(71) Applicants: Kingdomway Biotech. (Jiangsu) Co., Ltd, Jiangsu (CN); Xiamen Kingdomway Vitamin Inc., Fujian (CN); Xiamen Kingdomway Group Company, Fujian (CN)

(72) Inventors: Jun Zhu, Suzhou (CN); Jinchao Zhong, Fujian (CN); Fei Xu, Suzhou (CN); Chao Zhang, Suzhou (CN); Wenjie Lu, Suzhou (CN); Dan Li, Fujian (CN); Xiongzhi Huang, Fujian (CN)

(73) Assignees: Kingdomway Biotech. (Jiangsu) Co., Ltd, Jiangsu (CN); Xiamen Kingdomway Vitamin Inc., Fujian (CN); Xiamen Kingdomway Group Company, Fujian (CN)

( * ) Notice: Subject to any disclaimer, the term of this patent is extended or adjusted under 35 U.S.C. 154(b) by 412 days.

(21) Appl. No.: 18/488,519

(22) Filed: Oct. 17, 2023

(65) Prior Publication Data

US 2024/0218409 A1 Jul. 4, 2024

(30) Foreign Application Priority Data

Dec. 29, 2022 (CN) .......................... 202211709938.1

(51) Int. Cl.
*C12P 17/18* (2006.01)
*C12N 9/04* (2006.01)
*C12P 7/62* (2022.01)

(52) U.S. Cl.
CPC .......... *C12P 17/187* (2013.01); *C12N 9/0006* (2013.01); *C12P 7/62* (2013.01); *C12Y 101/01184* (2013.01)

(58) Field of Classification Search
CPC .. C12Y 101/01184; C12P 17/187; C12P 7/62; C12N 9/0006
See application file for complete search history.

(56) References Cited

U.S. PATENT DOCUMENTS 10,294,479 B2 * 5/2019 Xu et al. ................ C12N 15/52

FOREIGN PATENT DOCUMENTS

CN 114149324 A 3/2022

* cited by examiner

*Primary Examiner* — Manjunath N Rao
*Assistant Examiner* — Anthony Stapon
(74) *Attorney, Agent, or Firm* — Haynes and Boone, LLP

(57) ABSTRACT

The present invention provides a carbonyl reductase mutant, preparation method and use thereof, and a preparation method of ethyl (R)-6-hydroxy-8-chlorooctanoate. The carbonyl reductase mutant is a carbonyl reductase with amino acid mutation; the carbonyl reductase comprises an amino acid sequence as set forth in SEQ ID NO: 2; the amino acid mutation includes E101V, F214R or E101V/F214R. In the present invention, by introducing mutations on the basis of the original carbonyl reductase sequence, the enzyme activity is improved, the stereoselectivity is improved, and ethyl (R)-6-hydroxy-8-chlorooctanoate can be obtained with high yield and high purity under relatively mild conditions, which reduces the production cost and is suitable for industrial production.

20 Claims, 1 Drawing Sheet

Specification includes a Sequence Listing.

SEQUENCE LISTING

```
Sequence total quantity: 12
SEQ ID NO: 1           moltype = DNA  length = 993
FEATURE                Location/Qualifiers
source                 1..993
                       mol_type = other DNA
                       organism = synthetic construct
SEQUENCE: 1
atgatgagcg tctccgggtt cctcggatcc gcaacgctgg tcgcgttcgt ctcgcgaggc   60
gtgcatgtca gggcgactgt gcgttcccag tctaaagcag atgcttgggt tgctcaatac  120
cccgagtaca agcaccttat cgagtggtgc atcgttcccg acatcgcgaa agagggcgcg  180
ttcattgatg ccgtgaaagg cgttacgagg gtcgttcata ccgccagtcc tttccacttc  240
aactccacta ccccatccga cctcctcgat cctgccataa aaggaactct cagtattctc  300
gaagcggctc tcactgagcc ggcgatcaaa acggtcgtca tcacgtcttc agatgctgct  360
atccgtgatc acgataaggg ctggagagag ggctatacct acacttcggc cgattggaac  420
ccgttcacta tggaacaggc gttggcggag actaaccctc actcaatcta tgtcgcatcc  480
aaagcgctcg ccgagcgcgc cgcctggaaa ttcatggacg acaagcaccc ctcgttcacg  540
ctcacgacca tctgcccagt cctcatcctc ggtcccatgc tccaacccgt ctccaaactc  600
tccgacatga acctcagcac cacgatcgtg tgggacctct tccacaaacc tactgtgccg  660
gacacgtggg tgcctatgtt cgtcgacgtg agagattgcg ctctggcgca ctacgaagcg  720
acgttccgtc ccgtcgcggc ggggaaacgc tacctctgcg ctgcctccga acactattcc  780
gacgtcgacg tcgccatcgc gcttcgtgag gctttccctg aggagggtca caggatcccc  840
actggaggaa ataggccgac gaaccattat gggtgggatt cgaagccagc ggaggaagac  900
```

```
ctcggaatca agtggacgcc gttggccaag tgtgttgagg attgcgggaa acagttgttg   960
gagatggaaa aggctgagaa aggctccgca tga                                 993

SEQ ID NO: 2           moltype = AA  length = 330
FEATURE                Location/Qualifiers
source                 1..330
                       mol_type = protein
                       organism = synthetic construct
SEQUENCE: 2
MMSVSGFLGS ATLVAFVSRG VHVRATVRSQ SKADAWVAQY PEYKHLIEWC IVPDIAKEGA   60
FIDAVKGVTR VVHTASPFHF NSTTPSDLLD PAIKGTLSIL EAALTEPAIK TVVITSSDAA   120
IRDHDKGWRE GYTYTSADWN PFTMEQALAE TNPHSIYVAS KALAERAAWK FMDDKHPSFT   180
LTTICPVLIL GPMLQPVSKL SDMNLSTTIV WDLFHKPTVP DTWVPMFVDV RDCALAHYEA   240
TFRPVAAGKR YLCAASEHYS DVDVAIALRE AFPEEGHRIP TGGNRPTNHY GWDSKPAEED   300
LGIKWTPLAK CVEDCGKQLL EMEKAEKGSA                                     330

SEQ ID NO: 3           moltype = DNA  length = 38
FEATURE                Location/Qualifiers
source                 1..38
                       mol_type = other DNA
                       organism = synthetic construct
SEQUENCE: 3
aaggaactct cagtattctc gtagcggctc tcactgag                            38

SEQ ID NO: 4           moltype = DNA  length = 38
FEATURE                Location/Qualifiers
source                 1..38
                       mol_type = other DNA
                       organism = synthetic construct
SEQUENCE: 4
tacgagaata ctgagagttc cttttatggc aggatcga                            38

SEQ ID NO: 5           moltype = DNA  length = 38
FEATURE                Location/Qualifiers
source                 1..38
                       mol_type = other DNA
                       organism = synthetic construct
SEQUENCE: 5
ccacgatcgt gtgggacctc cgccacaaac ctactgtg                            38

SEQ ID NO: 6           moltype = DNA  length = 38
FEATURE                Location/Qualifiers
source                 1..38
                       mol_type = other DNA
                       organism = synthetic construct
SEQUENCE: 6
gcggaggtcc cacacgatcg tggtgctgag gttcatgt                            38

SEQ ID NO: 7           moltype = AA  length = 330
FEATURE                Location/Qualifiers
source                 1..330
                       mol_type = protein
                       organism = synthetic construct
SEQUENCE: 7
MMSVSGFLGS ATLVAFVSRG VHVRATVRSQ SKADAWVAQY PEYKHLIEWC IVPDIAKEGA   60
FIDAVKGVTR VVHTASPFHF NSTTPSDLLD PAIKGTLSIL VAALTEPAIK TVVITSSDAA   120
IRDHDKGWRE GYTYTSADWN PFTMEQALAE TNPHSIYVAS KALAERAAWK FMDDKHPSFT   180
LTTICPVLIL GPMLQPVSKL SDMNLSTTIV WDLFHKPTVP DTWVPMFVDV RDCALAHYEA   240
TFRPVAAGKR YLCAASEHYS DVDVAIALRE AFPEEGHRIP TGGNRPTNHY GWDSKPAEED   300
LGIKWTPLAK CVEDCGKQLL EMEKAEKGSA                                     330

SEQ ID NO: 8           moltype = DNA  length = 993
FEATURE                Location/Qualifiers
source                 1..993
                       mol_type = other DNA
                       organism = synthetic construct
SEQUENCE: 8
atgatgagcg tctccgggtt cctcggatcc gcaacgctgg tcgcgttcgt ctcgcgaggc   60
gtgcatgtca gggcgactgt gcgttcccag tctaaagcag atgcttgggt tgctcaatac   120
cccgagtaca agcaccttat cgagtggtgc atcgttcccg acatcgcgaa agagggcgcg   180
ttcattgatg ccgtgaaagg cgttacgagg gtcgttcata ccgccagtcc tttccacttc   240
aactccacta ccccatccga cctcctcgat cctgccataa aaggaactct cagtattctc   300
gtagcggctc tcactgagcc ggcgatcaaa acggtcgtca tcacgtcttc agatgctgct   360
atccgtgatc acgataaggg ctggagagag ggctatacct acacttcggc cgattggaac   420
ccgttcacta tggaacaggc gttggcggag actaaccctc actcaatcta tgtcgcatcc   480
aaagcgctcg ccgagcgcgc cgcctggaaa ttcatggacg acaagcaccc ctcgttcacg   540
ctcacgacca tctgcccagt cctcatcctc ggtcccatgc tccaacccgt ctccaaactc   600
tccgacatga acctcagcac cacgatcgtg tgggacctct ccacaaaacc tactgtgccg   660
gacacgtggg tgcctatgtt cgtcgacgtg agagattgcg ctctggcgca ctacgaagcg   720
```

```
acgttccgtc ccgtcgcggc ggggaaacgc tacctctgcg ctgcctccga acactattcc   780
gacgtcgacg tcgccatcgc gcttcgtgag gctttccctg aggagggtca caggatcccc   840
actggaggaa ataggccgac gaaccattat gggtgggatt cgaagccagc ggaggaagac   900
ctcggaatca agtggacgcc gttggccaag tgtgttgagg attgcgggaa acagttgttg   960
gagatggaaa aggctgagaa aggctccgca tga                                993
```

SEQ ID NO: 9          moltype = AA   length = 330
FEATURE               Location/Qualifiers
source                1..330
                      mol_type = protein
                      organism = synthetic construct
SEQUENCE: 9

```
MMSVSGFLGS ATLVAFVSRG VHVRATVRSQ SKADAWVAQY PEYKHLIEWC IVPDIAKEGA   60
FIDAVKGVTR VVHTASPFHF NSTTPSDLLD PAIKGTLSIL EAALTEPAIK TVVITSSDAA   120
IRDHDKGWRE GYTYTSADWN PFTMEQALAE TNPHSIYVAS KALAERAAWK FMDDKHPSFT   180
LTTICPVLIL GPMLQPVSKL SDMNLSTTIV WDLRHKPTVP DTWVPMFVDV RDCALAHYEA   240
TFRPVAAGKR YLCAASEHYS DVDVAIALRE AFPEEGHRIP TGGNRPTNHY GWDSKPAEED   300
LGIKWTPLAK CVEDCGKQLL EMEKAEKGSA                                    330
```

SEQ ID NO: 10         moltype = DNA   length = 993
FEATURE               Location/Qualifiers
source                1..993
                      mol_type = other DNA
                      organism = synthetic construct
SEQUENCE: 10

```
atgatgagcg tctccgggtt cctcggatcc gcaacgctgg tcgcgttcgt ctcgcgaggc   60
gtgcatgtca gggcgactgt gcgttcccag tctaaagcag atgcttgggt tgctcaatac   120
cccgagtaca agcaccttat cgagtggtgc atcgttcccg acatcgcgaa agagggcgcg   180
ttcattgatg ccgtgaaagg cgttacgagg gtcgttcata ccgccagtcc tttccacttc   240
aactccacta ccccatccga cctcctcgat cctgccataa aaggaactct cagtattctc   300
gaagcggctc tcactgagcc ggcgatcaaa acggtcgtca tcacgtcttc agatgctgct   360
atccgtgatc acgataaggg ctggagagag ggctatacct acacttcggc cgattggaac   420
ccgttcacta tggaacaggc gttggcggag actaaccctc actcaatcta tgtcgcatcc   480
aaagcgctcg ccgagcgcgc cgcctggaaa ttcatggacg acaagcaccc ctcgttcacg   540
ctcacgacca tctgcccagt cctcatcctc ggtcccatgc tccaacccgt ctccaaactc   600
tccgacatga acctcagcac cacgatcgtg tgggacctcc gccacaaacc tactgtgccg   660
gacacgtggg tgcctatgtt cgtcgacgtg agagattgcg ctctggcgca ctacgaagcg   720
acgttccgtc ccgtcgcggc ggggaaacgc tacctctgcg ctgcctccga acactattcc   780
gacgtcgacg tcgccatcgc gcttcgtgag gctttccctg aggagggtca caggatcccc   840
actggaggaa ataggccgac gaaccattat gggtgggatt cgaagccagc ggaggaagac   900
ctcggaatca agtggacgcc gttggccaag tgtgttgagg attgcgggaa acagttgttg   960
gagatggaaa aggctgagaa aggctccgca tga                                993
```

SEQ ID NO: 11         moltype = AA   length = 330
FEATURE               Location/Qualifiers
source                1..330
                      mol_type = protein
                      organism = synthetic construct
SEQUENCE: 11

```
MMSVSGFLGS ATLVAFVSRG VHVRATVRSQ SKADAWVAQY PEYKHLIEWC IVPDIAKEGA   60
FIDAVKGVTR VVHTASPFHF NSTTPSDLLD PAIKGTLSIL VAALTEPAIK TVVITSSDAA   120
IRDHDKGWRE GYTYTSADWN PFTMEQALAE TNPHSIYVAS KALAERAAWK FMDDKHPSFT   180
LTTICPVLIL GPMLQPVSKL SDMNLSTTIV WDLRHKPTVP DTWVPMFVDV RDCALAHYEA   240
TFRPVAAGKR YLCAASEHYS DVDVAIALRE AFPEEGHRIP TGGNRPTNHY GWDSKPAEED   300
LGIKWTPLAK CVEDCGKQLL EMEKAEKGSA                                    330
```

SEQ ID NO: 12         moltype = DNA   length = 993
FEATURE               Location/Qualifiers
source                1..993
                      mol_type = other DNA
                      organism = synthetic construct
SEQUENCE: 12

```
atgatgagcg tctccgggtt cctcggatcc gcaacgctgg tcgcgttcgt ctcgcgaggc   60
gtgcatgtca gggcgactgt gcgttcccag tctaaagcag atgcttgggt tgctcaatac   120
cccgagtaca agcaccttat cgagtggtgc atcgttcccg acatcgcgaa agagggcgcg   180
ttcattgatg ccgtgaaagg cgttacgagg gtcgttcata ccgccagtcc tttccacttc   240
aactccacta ccccatccga cctcctcgat cctgccataa aaggaactct cagtattctc   300
gtagcggctc tcactgagcc ggcgatcaaa acggtcgtca tcacgtcttc agatgctgct   360
atccgtgatc acgataaggg ctggagagag ggctatacct acacttcggc cgattggaac   420
ccgttcacta tggaacaggc gttggcggag actaaccctc actcaatcta tgtcgcatcc   480
aaagcgctcg ccgagcgcgc cgcctggaaa ttcatggacg acaagcaccc ctcgttcacg   540
ctcacgacca tctgcccagt cctcatcctc ggtcccatgc tccaacccgt ctccaaactc   600
tccgacatga acctcagcac cacgatcgtg tgggacctcc gccacaaacc tactgtgccg   660
gacacgtggg tgcctatgtt cgtcgacgtg agagattgcg ctctggcgca ctacgaagcg   720
acgttccgtc ccgtcgcggc ggggaaacgc tacctctgcg ctgcctccga acactattcc   780
gacgtcgacg tcgccatcgc gcttcgtgag gctttccctg aggagggtca caggatcccc   840
```

-continued

```
actggaggaa ataggccgac gaaccattat gggtgggatt cgaagccagc ggaggaagac   900
ctcggaatca agtggacgcc gttggccaag tgtgttgagg attgcgggaa acagttgttg   960
gagatggaaa aggctgagaa aggctccgca tga                                993
```

CARBONYL REDUCTASE MUTANT, PREPARATION METHOD AND USE THEREOF, AND PREPARATION METHOD OF ETHYL (R)-6-HYDROXY-8-CHLOROOCTANOATE

TECHNICAL FIELD

The present invention belongs to the technical field of protein engineering, and relates to a carbonyl reductase mutant, preparation method and use thereof, and preparation method of ethyl (R)-6-hydroxy-8-chlorooctanoate.

The instant application contains a Sequence Listing which has been submitted electronically in XML and is hereby incorporated by reference in its entirety. Said XML copy, created on Dec. 18, 2023, is named IEC230037-US_Sequence Listing.xml and is 18 kilobytes in size.

BACKGROUND ART

Ethyl 6-hydroxy-8-chlorooctanoate is an important organic intermediate, which is currently mainly used in the synthesis of certain drugs and drug intermediates, especially the synthesis of α-lipoic acid drug intermediates. Alpha-lipoic acid has antioxidant properties and is a vitamin-like compound that eliminates free radicals that accelerate aging and cause diseases. Wherein, (S)-α-lipoic acid has almost no oxidation activity, so optically pure (R)-α-lipoic acid has attracted much attention, and ethyl (R)-6-hydroxy-8-chlorooctanoate is used as a chiral precursor for the preparation of (R)-α-lipoic acid and is therefore of vital importance.

The main scheme for the synthesis of ethyl 6-hydroxy-8-chlorooctanoate is the method of MPV reduction of ethyl 6-hydroxy-8-oxo-octanoate (CN114149324A); in which methanol is used as solvent, and sodium borohydride is used for reduction; lipase is used for hydrolysis and resolution of racemic lipoic acid intermediate, ethyl 6-hydroxy-8-chlorooctanoate to prepare ethyl (R)-6-hydroxy-8-chlorooctanoate; (R)-enantiomer is obtained by kinetic resolution of racemic ethyl 6-hydroxy-8-chlorooctanoate by enzymatic acetylation reaction, etc. In this method, the product obtained by sodium borohydride reduction is a racemate, which is then resolved by lipase, and the theoretical maximum yield is only 50%, which is contrary to atomic economics, and there are many reaction steps, and the amount of three wastes generated is obviously not advantageous.

Therefore, in the art, it is expected to develop a method for preparing ethyl (R)-6-hydroxy-8-chlorooctanoate in high yield under milder conditions.

Contents of the Invention

Aiming at the deficiencies of the prior art, the object of the present invention is to provide a carbonyl reductase mutant, preparation method and use thereof, and a preparation method of ethyl (R)-6-hydroxy-8-chlorooctanoate. In the present invention, by introducing mutations on the basis of the original carbonyl reductase sequence, the enzyme activity is improved, the stereoselectivity is improved, and ethyl (R)-6-hydroxy-8-chlorooctanoate can be obtained with high yield and high purity under relatively mild conditions, which reduces the production cost and is suitable for industrial production.

To achieve the object of the present invention, the present invention adopts the following technical solutions:

In the first aspect, the present invention provides a carbonyl reductase mutant, the carbonyl reductase mutant is a carbonyl reductase with an amino acid mutation; the carbonyl reductase comprises an amino acid sequence as set forth in SEQ ID NO: 2;

the amino acid mutation is of the following: E101V, F214R or E101V/F214R.

```
SEQ ID NO: 2:
MMSVSGFLGSATLVAFVSRGVHVRATVRSQSKADAWVAQYPEYKHLIEW

CIVPDIAKEGAFIDAVKGVTRVVHTASPFHFNSTTPSDLLDPAIKGTLS

ILEAALTEPAIKTVVITSSDAAIRDHDKGWREGYTYTSADWNPFTMEQA

LAETNPHSIYVASKALAERAAWKFMDDKHPSFTLTTICPVLILGPMLQP

VSKLSDMNLSTTIVWDLFHKPTVPDTWVPMFVDVRDCALAHYEATFRPV

AAGKRYLCAASEHYSDVDVAIALREAFPEEGHRIPTGGNRPTNHYGWDS

KPAEEDLGIKWTPLAKCVEDCGKQLLEMEKAEKGSA.
```

In the present invention, by introducing the above-mentioned mutation into the carbonyl reductase, the activity and stereoselectivity of the enzyme are significantly improved, and ethyl (R)-6-hydroxyl-8-chlorooctanoate can be obtained with high yield and high purity under relatively mild conditions, which reduces the production cost and is suitable for industrialized production.

Preferably, the carbonyl reductase has a coding sequence comprising a nucleotide sequence as set forth in SEQ ID NO: 1.

```
SEQ ID NO: 1:
ATGATGAGCGTCTCCGGGTTCCTCGGATCCGCAACGCTGGTCGCGTTCG

TCTCGCGAGGCGTGCATGTCAGGGCGACTGTGCGTTCCCAGTCTAAAGC

AGATGCTTGGGTTGCTCAATACCCCGAGTACAAGCACCTTATCGAGTGG

TGCATCGTTCCCGACATCGCGAAAGAGGGCGCGTTCATTGATGCCGTGA

AAGGCGTTACGAGGGTCGTTCATACCGCCAGTCCTTTCCACTTCAACTC

CACTACCCCATCCGACCTCCTCGATCCTGCCATAAAAGGAACTCTCAGT

ATTCTCGAAGCGGCTCTCACTGAGCCGGCGATCAAAACGGTCGTCATCA

CGTCTTCAGATGCTGCTATCCGTGATCACGATAAGGGCTGGAGAGAGGG

CTATACCTACACTTCGGCCGATTGGAACCCGTTCACTATGGAACAGGCG

TTGGCGGAGACTAACCCTCACTCAATCTATGTCGCATCCAAAGCGCTCG

CCGAGCGCGCCGCCTGGAAATTCATGGACGACAAGCACCCCTCGTTCAC

GCTCACGACCATCTGCCCAGTCCTCATCCTCGGTCCCATGCTCCAACCC

GTCTCCAAACTCTCCGACATGAACCTCAGCACCACGATCGTGTGGGACC

TCTTCCACAAACCTACTGTGCCGGACACGTGGGTGCCTATGTTCGTCGA

CGTGAGAGATTGCGCTCTGGCGCACTACGAAGCGACGTTCCGTCCCGTC

GCGGCGGGGAAACGCTACCTCTGCGCTGCCTCCGAACACTATTCCGACG

TCGACGTCGCCATCGCGCTTCGTGAGGCTTTCCCTGAGGAGGGTCACAG

GATCCCCACTGGAGGAAATAGGCCGACGAACCATTATGGGTGGGATTCG

AAGCCAGCGGAGGAAGACCTCGGAATCAAGTGGACGCCGTTGGCCAAGT
```

-continued

GTGTTGAGGATTGCGGGAAACAGTTGTTGGAGATGGAAAAGGCTGAGAA

AGGCTCCGCATGA.

Preferably, the carbonyl reductase is derived from *Pseudohyphozyma bogoriensis*.

Preferably, the E101V mutation has a forward primer nucleotide sequence (E101V-F) comprising a sequence as set forth in SEQ ID NO: 3, and a reverse primer nucleotide sequence (E101V-R) comprising a sequence as set forth in SEQ ID NO: 4.

```
SEQ ID NO: 3:
AAGGAACTCTCAGTATTCTCGTAGCGGCTCTCACTGAG.

SEQ ID NO: 4:
TACGAGAATACTGAGAGTTCCTTTTATGGCAGGATCGA.
```

Preferably, the F214R mutation has a forward primer nucleotide sequence (F214R-F) comprising a sequence as set forth in SEQ ID NO: 5, and a reverse primer nucleotide sequence (F214R-R) comprising a sequence as set forth in SEQ ID NO: 6.

```
SEQ ID NO: 5:
CCACGATCGTGTGGGACCTCCGCCACAAACCTACTGTG.

SEQ ID NO: 6:
GCGGAGGTCCCACACGATCGTGGTGCTGAGGTTCATGT.
```

After mutation, the E101V mutant comprises an amino acid sequence as set forth in SEQ ID NO: 7, and the E101V mutant has a coding sequence comprising a nucleotide sequence as set forth in SEQ ID NO: 8.

The F214R mutant comprises an amino acid sequence as set forth in SEQ ID NO: 9, and the F214R mutant has a coding sequence comprising a nucleotide sequence as set forth in SEQ ID NO: 10.

The E101V/F214R mutant comprises an amino acid sequence as set forth in SEQ ID NO: 11, and the E101V/F214R mutant has a coding sequence comprising a nucleotide sequence as set forth in SEQ ID NO: 12.

```
SEQ ID NO: 7:
MMSVSGFLGSATLVAFVSRGVHVRATVRSQSKADAWVAQYPEYKHLIEW

CIVPDIAKEGAFIDAVKGVTRVVHTASPFHFNSTTPSDLLDPAIKGTLS

ILVAALTEPAIKTVVITSSDAAIRDHDKGWREGYTYTSADWNPFTMEQA

LAETNPHSIYVASKALAERAAWKFMDDKHPSFTLTTICPVLILGPMLQP

VSKLSDMNLSTTIVWDLFHKPTVPDTWVPMFVDVRDCALAHYEATFRPV

AAGKRYLCAASEHYSDVDVAIALREAFPEEGHRIPTGGNRPTNHYGWDS

KPAEEDLGIKWTPLAKCVEDCGKQLLEMEKAEKGSA.

SEQ ID NO: 8:
ATGATGAGCGTCTCCGGGTTCCTCGGATCCGCAACGCTGGTCGCGTTCG

TCTCGCGAGGCGTGCATGTCAGGGCGACTGTGCGTTCCCAGTCTAAAGC

AGATGCTTGGGTTGCTCAATACCCCGAGTACAAGCACCTTATCGAGTGG

TGCATCGTTCCCGACATCGCGAAAGAGGGCGCGTTCATTGATGCCGTGA

AAGGCGTTACGAGGGTCGTTCATACCGCCAGTCCTTTCCACTTCAACTC

CACTACCCCATCCGACCTCCTCGATCCTGCCATAAAAGGAACTCTCAGT
```

-continued

ATTCTCGTAGCGGCTCTCACTGAGCCGGCGATCAAAACGGTCGTCATCA

CGTCTTCAGATGCTGCTATCCGTGATCACGATAAGGGCTGGAGAGAGGG

CTATACCTACACTTCGGCCGATTGGAACCCGTTCACTATGGAACAGGCG

TTGGCGGAGACTAACCCTCACTCAATCTATGTCGCATCCAAAGCGCTCG

CCGAGCGCGCCGCCTGGAAATTCATGGACGACAAGCACCCCTCGTTCAC

GCTCACGACCATCTGCCCAGTCCTCATCCTCGGTCCCATGCTCCAACCC

GTCTCCAAACTCTCCGACATGAACCTCAGCACCACGATCGTGTGGGACC

TCTTCCACAAACCTACTGTGCCGGACACGTGGGTGCCTATGTTCGTCGA

CGTGAGAGATTGCGCTCTGGCGCACTACGAAGCGACGTTCCGTCCCGTC

GCGGCGGGGAAACGCTACCTCTGCGCTGCCTCCGAACACTATTCCGACG

TCGACGTCGCCATCGCGCTTCGTGAGGCTTTCCCTGAGGAGGGTCACAG

GATCCCCACTGGAGGAAATAGGCCGACGAACCATTATGGGTGGGATTCG

AAGCCAGCGGAGGAAGACCTCGGAATCAAGTGGACGCCGTTGGCCAAGT

GTGTTGAGGATTGCGGGAAACAGTTGTTGGAGATGGAAAAGGCTGAGAA

AGGCTCCGCATGA.

```
SEQ ID NO: 9:
MMSVSGFLGSATLVAFVSRGVHVRATVRSQSKADAWVAQYPEYKHLIEW

CIVPDIAKEGAFIDAVKGVTRVVHTASPFHFNSTTPSDLLDPAIKGTLS

ILEAALTEPAIKTVVITSSDAAIRDHDKGWREGYTYTSADWNPFTMEQA

LAETNPHSIYVASKALAERAAWKFMDDKHPSFTLTTICPVLILGPMLQP

VSKLSDMNLSTTIVWDLRHKPTVPDTWVPMFVDVRDCALAHYEATFRPV

AAGKRYLCAASEHYSDVDVAIALREAFPEEGHRIPTGGNRPTNHYGWDS

KPAEEDLGIKWTPLAKCVEDCGKQLLEMEKAEKGSA.

SEQ ID NO: 10:
ATGATGAGCGTCTCCGGGTTCCTCGGATCCGCAACGCTGGTCGCGTTCG

TCTCGCGAGGCGTGCATGTCAGGGCGACTGTGCGTTCCCAGTCTAAAGC

AGATGCTTGGGTTGCTCAATACCCCGAGTACAAGCACCTTATCGAGTGG

TGCATCGTTCCCGACATCGCGAAAGAGGGCGCGTTCATTGATGCCGTGA

AAGGCGTTACGAGGGTCGTTCATACCGCCAGTCCTTTCCACTTCAACTC

CACTACCCCATCCGACCTCCTCGATCCTGCCATAAAAGGAACTCTCAGT

ATTCTCGAAGCGGCTCTCACTGAGCCGGCGATCAAAACGGTCGTCATCA

CGTCTTCAGATGCTGCTATCCGTGATCACGATAAGGGCTGGAGAGAGGG

CTATACCTACACTTCGGCCGATTGGAACCCGTTCACTATGGAACAGGCG

TTGGCGGAGACTAACCCTCACTCAATCTATGTCGCATCCAAAGCGCTCG

CCGAGCGCGCCGCCTGGAAATTCATGGACGACAAGCACCCCTCGTTCAC

GCTCACGACCATCTGCCCAGTCCTCATCCTCGGTCCCATGCTCCAACCC

GTCTCCAAACTCTCCGACATGAACCTCAGCACCACGATCGTGTGGGACC

TCCGCCACAAACCTACTGTGCCGGACACGTGGGTGCCTATGTTCGTCGA

CGTGAGAGATTGCGCTCTGGCGCACTACGAAGCGACGTTCCGTCCCGTC

GCGGCGGGGAAACGCTACCTCTGCGCTGCCTCCGAACACTATTCCGACG

TCGACGTCGCCATCGCGCTTCGTGAGGCTTTCCCTGAGGAGGGTCACAG

GATCCCCACTGGAGGAAATAGGCCGACGAACCATTATGGGTGGGATTCG
```

5

-continued

```
AAGCCAGCGGAGGAAGACCTCGGAATCAAGTGGACGCCGTTGGCCAAGT

GTGTTGAGGATTGCGGGAAACAGTTGTTGGAGATGGAAAAGGCTGAGAA

AGGCTCCGCATGA.

SEQ ID NO: 11:
MMSVSGFLGSATLVAFVSRGVHVRATVRSQSKADAWVAQYPEYKHLIEW

CIVPDIAKEGAFIDAVKGVTRVVHTASPFHFNSTTPSDLLDPAIKGTLS

ILVAALTEPAIKTVVITSSDAAIRDHDKGWREGYTYTSADWNPFTMEQA

LAETNPHSIYVASKALAERAAWKFMDDKHPSFTLTTICPVLILGPMLQP

VSKLSDMNLSTTIVWDLRHKPTVPDTWVPMFVDVRDCALAHYEATFRPV

AAGKRYLCAASEHYSDVDVAIALREAFPEEGHRIPTGGNRPTNHYGWDS

KPAEEDLGIKWTPLAKCVEDCGKQLLEMEKAEKGSA.

SEQ ID NO: 12:
ATGATGAGCGTCTCCGGGTTCCTCGGATCCGCAACGCTGGTCGCGTTCG

TCTCGCGAGGCGTGCATGTCAGGGCGACTGTGCGTTCCCAGTCTAAAGC

AGATGCTTGGGTTGCTCAATACCCCGAGTACAAGCACCTTATCGAGTGG

TGCATCGTTCCCGACATCGCGAAAGAGGGCGCGTTCATTGATGCCGTGA

AAGGCGTTACGAGGGTCGTTCATACCGCCAGTCCTTTCCACTTCAACTC

CACTACCCCATCCGACCTCCTCGATCCTGCCATAAAAGGAACTCTCAGT

ATTCTCGTAGCGGCTCTCACTGAGCCGGCGATCAAAACGGTCGTCATCA

CGTCTTCAGATGCTGCTATCCGTGATCACGATAAGGGCTGGAGAGAGGG

CTATACCTACACTTCGGCCGATTGGAACCCGTTCACTATGGAACAGGCG

TTGGCGGAGACTAACCCTCACTCAATCTATGTCGCATCCAAAGCGCTCG

CCGAGCGCGCCGCCTGGAAATTCATGGACGACAAGCACCCCTCGTTCAC

GCTCACGACCATCTGCCCAGTCCTCATCCTCGGTCCCATGCTCCAACCC

GTCTCCAAACTCTCCGACATGAACCTCAGCACCACGATCGTGTGGGACC

TCCGCCACAAACCTACTGTGCCGGACACGTGGGTGCCTATGTTCGTCGA

CGTGAGAGATTGCGCTCTGGCGCACTACGAAGCGACGTTCCGTCCCGTC

GCGGCGGGGAAACGCTACCTCTGCGCTGCCTCCGAACACTATTCCGACG

TCGACGTCGCCATCGCGCTTCGTGAGGCTTTCCCTGAGGAGGGTCACAG

GATCCCCACTGGAGGAAATAGGCCGACGAACCATTATGGGTGGGATTCG

AAGCCAGCGGAGGAAGACCTCGGAATCAAGTGGACGCCGTTGGCCAAGT

GTGTTGAGGATTGCGGGAAACAGTTGTTGGAGATGGAAAAGGCTGAGAA

AGGCTCCGCATGA.
```

In a second aspect, the present invention provides a nucleic acid molecule, which encodes the carbonyl reductase mutant described in the first aspect.

In a third aspect, the present invention provides an expression vector, which comprises at least one copy of the nucleic acid molecule described in the second aspect.

In the fourth aspect, the present invention provides a carbonyl reductase mutant transformant, which is a genetically engineered strain expressing the carbonyl reductase mutant described in the first aspect.

Preferably, the carbonyl reductase mutant transformant comprises the nucleic acid molecule described in the second aspect.

Preferably, the carbonyl reductase mutant transformant comprises the expression vector described in the third aspect.

Preferably, the genetically engineered strain comprises any one of *Escherichia coli*, *Pichia pastoris* or *Bacillus subtilis*.

In the fifth aspect, the present invention provides a method for preparing the carbonyl reductase mutant described in the first aspect, the preparation method comprising:

constructing an expression vector, transforming into a recipient cell, and constructing a carbonyl reductase mutant transformant;

Culturing the carbonyl reductase mutant transformant, and collecting the culture to obtain the carbonyl reductase mutant.

Preferably, the vector is a vector of pET series, preferably pET-28a.

As a preferred technical solution, the preparation method of the carbonyl reductase mutant of the present invention specifically comprises the following steps:

ligating and recombining the nucleic acid molecule encoding the carbonyl reductase mutant into an expression vector pET-28a(+) by restriction enzyme digestion, and transforming into a host cell BL21 (DE3); screening a positive clone to obtain the carbonyl reductase mutant transformant;

placing the carbonyl reductase mutant transformant in a LB liquid medium for activation, then transferring into the LB liquid medium for cultivation, and finally collecting cells after fermentation and cultivation; and breaking the bacterial cells to obtain a carbonyl reductase mutant enzyme solution.

In a sixth aspect, the present invention provides a use of the carbonyl reductase mutant described in the first aspect in catalyzing a carbonyl reduction reaction;

preferably, the carbonyl reduction reaction uses a substrate comprising ethyl 6-oxo-8-chlorooctanoate.

In another aspect, the present invention provides a method for catalyzing a carbonyl reduction reaction, including a step of using the carbonyl reductase mutant described in the first aspect in catalyzing a carbonyl reduction reaction;

preferably, the carbonyl reduction reaction uses a substrate including ethyl 6-oxo-8-chlorooctanoate.

In the seventh aspect, the present invention provides a method for preparing ethyl (R)-6-hydroxy-8-chlorooctanoate, the method comprising the following steps:

mixing the carbonyl reductase mutant described in the first aspect with a reaction solution containing ethyl 6-oxo-8-chlorooctanoate, and reacting to obtain ethyl (R)-6-hydroxy-8-chlorooctanoate.

Preferably, the ethyl 6-oxo-8-chlorooctanoate in the reaction system has a mass percent concentration of 4% to 30%.

Preferably, the carbonyl reductase mutant is used in an amount of 5% to 30%, such as 5%, 8%, 10%, 15%, 18%, 20%, 23%, 25%, 28% or 30%, by weight of ethyl 6-oxo-8-chlorooctanoate.

Preferably, the reaction solution further comprises includes glucose dehydrogenase, coenzyme and glucose;

Preferably, the glucose dehydrogenase in the reaction system is used in an amount of 3% to 10%, such as 3%, 5%, 8%, 9% or 10%, by weight of ethyl 6-oxo-8-chlorooctanoate.

Preferably, the coenzyme is NADP$^+$;

Preferably, the coenzyme is used in an amount of $1/10,000$ to $5/10,000$, such as $1/10,000$, $2/10,000$, $3/10,000$, or $4/10,000$ or $5/10,000$, by weight of ethyl 6-oxo-8-chlorooctanoate.

Preferably, the glucose is used in an amount 0.9 to 2 times, such as 0.9 times, 1 time, 1.3 times, 1.5 times, 1.8 times or 2 times, the weight of ethyl 6-oxo-8-chlorooctanoate.

Preferably, the solvent of the reaction is Tris-HCl buffer, phosphate buffer, triethanolamine hydrochloride buffer, sodium acetate buffer or Tris-phosphate buffer, preferably Tris-HCl buffer.

Preferably, the reaction is performed at pH 6.0 to 7.5 (e.g., 6.0, 6.2, 6.4, 6.8, 7.0, 7.2 or 7.5).

Preferably, the reaction is performed in the presence of a cosolvent, and the cosolvent is preferably any one or a combination of at least two of ethanol, propanol, isopropanol, DMF, DMSO, polyethylene glycol or Tween 80. Ethanol is preferred.

Preferably, the cosolvent in the reaction system is used in a volume percentage of 5% to 10%, such as 5%, 6%, 7%, 8%, 9% or 10%, by volume of the solvent.

Preferably, the reaction is performed at a temperature of 20° C. to 35° C. (e.g., 20° C., 23° C., 25° C., 28° C., 30° C., 33° C. or 35° C.), and the reaction is performed for a time of 4 to 24 h (e.g., 4 h, 6 h, 8 h, 10 h, 12 h, 15 h, 18 h, 20 h, 22 h or 24 h).

In the eighth aspect, the present invention provides a use of the carbonyl reductase mutant described in the first aspect or the carbonyl reductase mutant transformant described in the fourth aspect or the method described in the seventh aspect in the manufacture of (R)-α-lipoic acid.

In another aspect, the present invention provides a method for manufacturing (R)-α-lipoic acid, including the following steps:

(1) preparing ethyl (R)-6-hydroxy-8-chlorooctanoate by using the carbonyl reductase mutant described in the first aspect or the carbonyl reductase mutant transformant described in the fourth aspect, and (2) preparing (R)-α-lipoic acid from the ethyl (R)-6-hydroxy-8-chlorooctanoate.

In another aspect, the present invention provides a method for manufacturing (R)-α-lipoic acid, including the following steps:

1) preparing ethyl (R)-6-hydroxy-8-chlorooctanoate via the method described in the seventh aspect, and 2) preparing (R)-α-lipoic acid from the ethyl (R)-6-hydroxy-8-chlorooctanoate.

Compared with the prior art, the present invention has the following beneficial effects:

The carbonyl reductase mutant of the present invention introduces a mutation based on the original carbonyl reductase sequence, so that the enzyme activity is improved, the stereoselectivity is improved, and ethyl (R)-6-hydroxy-8-chlorooctanote can be obtained with high yield and high purity under mild conditions, which reduces the production cost and is suitable for industrial production.

BRIEF DESCRIPTION OF THE DRAWINGS

FIG. 1 shows a schematic diagram of the reaction for preparing ethyl (R)-6-hydroxyl-8-chlorooctanote in the present invention.

SPECIFIC MODELS FOR CARRYING OUT THE INVENTION

The technical solutions of the present invention will be further described below through specific models. It should be clear to those skilled in the art that the examples are only for helping to understand the present invention, and should not be regarded as specific limitations on the present invention.

Example 1: Construction of Carbonyl Reductase Mutant

Using an original carbonyl reductase nucleotide sequence (as set forth in SEQ ID NO: 2) of *Pseudohyphozyma bogoriensis* genome (GenBank: JALBUQ010000056.1) as a template, NdeI and XhoI (purchased from New England Biolabs, and operated according to the instructions) were used for the recombination into pET28a vector. The recombined vector was transformed into trans 5a competent cells (purchased from TransGen Biotech Co., Ltd.), spread on an LB agar plate containing 50 μg/mL kana resistance and cultured overnight at 37° C. to obtain the recombinant strain PB-CR0 with the original carbonyl reductase plasmid.

The PB-CR0 monoclone was picked and placed into an LB liquid medium containing 50 μg/mL kana resistance, and cultured at 37° C. and 200 rpm for 8 hours; and after culture, the recombinant plasmid with original carbonyl reductase was extracted by plasmid extraction kit. The mutation primers (SEQ ID NO: 3-6) were used to perform single-point mutation amplification PCR, respectively, and Takara Primestar max high-fidelity polymerase (purchased from Takara Company) was used for amplification, in which the PCR program comprised: 98° C. pre-denaturation for 3 minutes, 30 amplification cycles (98° C. 10 s, 55° C. 5 s, 72° C. 70 s), 72° C. 10 min. The amplification product was digested with DpnI at 37° C. for 1 h to remove the template; the mutant plasmid was transformed into BL21(DE3) competent cells, spread on an LB agar plate containing 50 μg/mL kana resistance and cultured overnight at 37° C. to obtain recombinant strains PB-CR1 (E101V) and PB-CR2 (F214R) with carbonyl reductase single-point mutation plasmids.

The monoclones of PB-CR1 and PB-CR2 were separately picked and placed into an LB liquid medium containing 50 μg/mL kana resistance, and cultured at 37° C. and 200 rpm for 8 hours, after the culture, the bacterial solutions were subjected to PCR identification and sequencing verification, and the strain PB-CR1 with the correct sequencing result was continued to undergo other different point mutations to obtain a multi-point mutation recombinant strain PB-CR3 (E101V/F214R), and each of the recombinant strains PB-CR1/2/3 was used for fermentation expression.

A single colony of each recombinant strain was picked, inoculated into 5 mL of an LB liquid medium containing 50 μg/mL kana resistance, and cultured on a shaker at 200 rpm and 37° C. for 8 hours. The seed liquid was taken at an inoculum amount of 2% and transferred into 50 mL of a TB liquid medium containing 50 μg/mL kana resistance, cultured on a shaker at 200 rpm and 37° C. for 2 hours, until the OD600 reached above 0.6, then 0.1 mmol/L IPTG was added, cooled down to 30° C. and continuously cultured for 16 hours; after centrifugation at 4° C. and 10,000 rpm for 15 minutes, the bacterial cells were collected, added with 15 mL of 50 mmol/L disodium hydrogen phosphate-sodium dihydrogen phosphate buffer and resuspended, the bacterial cells were disrupted by an ultrasonic breaker, and centrifuged at 4° C. and 10,000 rpm for 15 minutes to leave a supernatant as carbonyl reductase enzyme solution.

Example 2: Preparation of Ethyl (R)-6-Hydroxy-8-Chlorooctanoate Under Catalysis of Carbonyl Reductase In four 100 mL centrifuge tubes, 5 g of ethyl 6-oxo-8-chlorooctanoate, 2.5 mL of ethanol solution, 50 mL of Tris-HCl buffer solution (pH7.0, 100 mM) and 5 g of glucose were added, respectively, and then added with 0.5 g of different carbonyl reductase enzyme solutions, 0.2 g of GDH enzyme solution, 2.5 mg of NADP$^+$ dry powder to different tubes for reaction, the reaction system was maintained at a pH around 7.0, and shaken at 25° C. and 200 rpm for 8 hours, and samples were taken to measure conversion rate and ee value. The results were shown in Table 1.

Detection of Conversion Rate by Gas Chromatography:

Detection instrument: Shimadzu gas chromatograph with hydrogen flame ionization detector;

Chromatographic column: CP-Chirasil Dex CB (25 m*0.32 mm*0.25 μm);

Column flow rate of chromatographic column: 2 mL/min; column temperature of chromatographic column: using an initial temperature of 140° C., keeping for 2 min, increasing the temperature to 200° C. at 4° C./min, keeping for 5 min; injection volume: 1 μL; detector temperature: 270° C.; Sample port temperature: 270° C.; split ratio: 50:1.

Detection of Chirality:

Product purification: 200 μL of the reaction solution was taken, and extracted with 1000 μL of ethyl acetate, the organic layer was dried over magnesium sulfate, and used to detect ee value.

Instrument: Shimadzu gas chromatograph with hydrogen flame ionization detector;

Chromatographic column: CYCLOSIL-B (30 m*0.25 mm*0.25 μm);

Column flow rate: 1 mL/min;

Chromatographic column temperature: using an initial temperature of 160° C., keeping for 2 min, increasing the temperature to 190° C. at 1° C./min, keeping for 2 min, increasing the temperature to 220° C. at 20° C./min, keeping for 2 min;

Injection volume; 0.2 μL;

Detector temperature: 270° C.;

Injection port temperature: 270° C.;

Split ratio: 50:1;

ee value calculation formula: ee %=([R]−[S]/[R]+[S]) *100%.

TABLE 1

| Name | Source species | Conversion rate | ee value |
|---|---|---|---|
| Carbonyl reductase mutant (E101V/F214R) | Pseudohyphozyma bogoriensis | 90.62% | 99.84% |
| Carbonyl reductase mutant (E101V) | | 67.34% | 99.23% |
| Carbonyl reductase mutant (F214R) | | 54.23% | 95.16% |
| Original carbonyl reductase | | 26.95% | 87.58% |

It could be seen from Table 1 that the carbonyl reductase mutant derived from Pseudohyphozyma bogoriensis had a significantly improved enzymatic activity compared with the original carbonyl reductase, which could significantly increase the conversion rate of the product, improve the stereoselectivity, and increase the ee value of the product. Especially, the mutant E101V/F214R showed conversion rate of 90.62%, and ee value of 99.84%.

Example 3: Preparation of Ethyl (R)-6-Hydroxyl-8-Chlorooctanoate Under Catalysis of Carbonyl Reductase In four 100 mL centrifuge tubes, 15 g of ethyl 6-oxo-8-chlorooctanoate, 2.5 mL of DMSO solution, 50 mL of phosphate buffer solution (pH7.2, 100 mM) and 20 g of glucose were added, respectively, and then added with 0.8 g of different carbonyl reductase enzyme solutions, 0.8 g of GDH enzyme solution, 5 mg of NADP$^+$ dry powder to different tubes for reaction, the reaction system was maintained at a pH around 7.2, and shaken at 30° C. and 200 rpm for 8 hours, and samples were taken to measure conversion rate and ee value. The results were shown in Table 2.

TABLE 2

| Name | Source species | Conversion rate | ee value |
|---|---|---|---|
| Carbonyl reductase mutant (E101V/F214R) | Pseudohyphozyma bogoriensis | 87.63% | 99.54% |
| Carbonyl reductase mutant (E101V) | | 60.18% | 99.17% |
| Carbonyl reductase mutant (F214R) | | 48.65% | 95.33% |
| Original carbonyl reductase | | 21.79% | 86.77% |

Example 4: Preparation of Ethyl (R)-6-Hydroxy-8-Chlorooctanoate Catalyzed by Carbonyl Reductase In four 100 mL centrifuge tubes, 2 g of ethyl 6-oxo-8-chlorooctanoate, 2.5 mL of Tween 90 solution, 50 mL of sodium acetate buffer solution (pH6.0, 100 mM) and 2.5 g of glucose were added, respectively, and then added with 0.2 g of different carbonyl reductase enzyme solutions, 0.15 g of GDH enzyme solution, 1.0 mg of NADP$^+$ dry powder to different tubes for reaction, the reaction system was maintained at a pH around 6.0, and shaken at 20° C. and 200 rpm for 8 hours, and samples were taken to measure conversion rate and ee value. The results were shown in Table 3.

TABLE 3

| Name | Source species | Conversion rate | ee value |
|---|---|---|---|
| Carbonyl reductase mutant (E101V/F214R) | Pseudohyphozyma bogoriensis | 75.32% | 99.62% |
| Carbonyl reductase mutant (E101V) | | 57.32% | 99.19% |
| Carbonyl reductase mutant (F214R) | | 44.66% | 95.14% |
| Original carbonyl reductase | | 16.25% | 84.68% |

Example 5: Preparation of Ethyl (R)-6-Hydroxyl-8-Chlorooctanoate Catalyzed by Carbonyl Reductase In four 100 mL centrifuge tubes, 5 g of ethyl 6-oxo-8-chlorooctanoate, 2.5 mL of polyethylene glycol solution, 50 mL of triethanolamine hydrochloride buffer solution (pH7.0, 100 mM) and 7.5 g of glucose were added, respectively, and then added with 0.5 g of different carbonyl reductase enzyme solutions, 0.2 g of GDH enzyme solution, 1.5 mg of NADP$^+$ dry powder to different tubes for reaction, the reaction system was maintained at a pH around 7.0, and shaken at 20° C. and 200 rpm for 8 hours, and samples were taken to measure conversion rate and ee value. The results were shown in Table 4.

TABLE 4

| Name | Source species | Conversion rate | ee value |
|---|---|---|---|
| Carbonyl reductase mutant (E101V/F214R) | Pseudohyphozyma bogoriensis | 88.89% | 99.64% |
| Carbonyl reductase mutant (E101V) | | 62.54% | 99.17% |
| Carbonyl reductase mutant (F214R) | | 50.28% | 94.87% |
| Original carbonyl reductase | | 25.33% | 85.95% |

Example 6: Effects of Different Temperatures on Reduction Reaction

In 100 mL three-necked flasks, 5 g of crude ethyl 6-oxo-8-chlorooctanoate, 2.5 mL of ethanol solution, 50 mL of Tris-HCl buffer solution (pH7.0, 100 mM) and 5 g of glucose were added in order, then stirred, and added to the flasks with 0.5 g of carbonyl reductase mutant enzyme solution (derived from carbonyl reductase mutant E101V/F214R), 0.2 g of GDH enzyme solution, 2.5 mg of NADP+ dry powder for reaction, in which the reaction temperature was controlled at 20° C., 30° C., 35° C., and 40° C., respectively, and the pH of the reaction system was maintained at around 7.0. After 4 hours of reaction, the corresponding conversion rates were 59.26%, 97.88%, 86.72%, 0.25%, respectively; after 7.5 hours of reaction, the corresponding conversion rates were 78.00%, 100%, 0.45%, respectively, and the ee values of the products were 99.24%, 99.35% %, 99.34%, 99.07%, respectively. It could be seen that the carbonyl reductase mutant of the present invention could realize the preparation of ethyl (R)-6-hydroxy-8-chlorooctanoate under relatively mild conditions.

Example 7: Effects of Different pH Values on Reduction Reaction

In 100 mL three-neck flasks, 5 g of crude ethyl 6-oxo-8-chlorooctanoate, 2.5 mL of ethanol solution, 50 mL of Tris-HCl buffer solution (pH7.0, 100 mM) and 5 g of glucose were added in order, then stirred, and added to the flasks with 0.5 g of carbonyl reductase mutant enzyme solution (derived from carbonyl reductase mutant E101V/

F214R), 0.2 g of GDH enzyme solution, 2.5 mg of NADP+ dry powder for reaction, the reaction temperature was controlled at 30° C., and the pH of the reaction system was maintained at 6.0, 7.0, and 8.0, respectively. After 4 hours of reaction, the corresponding conversion rates were 72.75%, 97.88%, and 1.04%, respectively; after 7.5 hours of reaction, the corresponding conversion rates were 97.08%, 100%, and 2.18%, respectively, and the ee values of the products were 99.18%, 99.25%, and 99.07%, respectively.

Example 8: Effects of Different Amounts of Carbonyl Reductase on Reduction Reaction In 100 mL three-neck flasks, 5 g of crude ethyl 6-oxo-8-chlorooctanoate, 2.5 mL of ethanol solution, 50 mL of Tris-HCl buffer solution (pH7.0, 100 mM) and 5 g of glucose were added in order, then stirred, and added to the flasks with carbonyl reductase enzyme solution (derived from carbonyl reductase mutant E101V/F214R), 0.2 g of GDH enzyme solution, 2.5 mg of NADP+ dry powder for reaction, the reaction temperature was controlled at 30° C., the reaction system pH was maintained at 7.0, in which the amounts of carbonyl reductase enzyme solution were controlled at 35%, 30%, 20%, 10%, 5%, and 3% of the substrate, respectively. After 4 hours of reaction, the corresponding conversion rates were 98.72%, 99.01%, 98.12%, 91.50%, 51.65%, 31.25%, respectively; after 7.5 hours of reaction, the corresponding conversion rates were 99.16%, 99.89%, 99.92%, 99.87%, 81.42%, 45.07%, respectively, the corresponding product yields were 89.77%, 90.02%, 86.31%, 85.52%, 80.27%, 44.15%, respectively; and the ee values of the products were 99.45%, 99.53%, 99.60%, 99.45%, 99.25%, 99.03%, respectively.

The applicant declares that the present invention illustrates the process method of the present invention through the above examples, but the present invention is not limited to the above process steps, that is, it does not mean that the present invention must rely on the above process steps to be implemented. Those skilled in the art should understand that any improvement of the present invention, the equivalent replacement of the selected raw materials in the present invention, the addition of auxiliary components, the selection of specific methods, etc., all fall within the scope of protection and disclosure of the present invention.

What is claimed is:

1. A carbonyl reductase mutant comprising an amino acid mutation;
    wherein the carbonyl reductase comprises the amino acid sequence of SEQ ID NO: 2, and the amino acid mutation comprises E101V, F214R or both E101V and F214R.

2. The carbonyl reductase mutant according to claim 1, which is derived from a carbonyl reductase derived from *Pseudohyphozyma bogoriensis*.

3. The carbonyl reductase mutant of claim 1, which is expressed by a genetically engineered bacterial strain.

4. The carbonyl reductase mutant of claim 3, wherein the genetically engineered bacterial strain comprises any one of *Escherichia coli*, *Pichia pastoris* or *Bacillus subtilis*.

5. A nucleotide sequence encoding the carbonyl reductase mutant according to claim 1.

6. The nucleotide sequence according to claim 5, which comprises, SEQ ID NO: 8, SEQ ID NO: 10, or SEQ ID NO: 12.

7. An expression vector comprising at least one copy of the nucleotide sequence according to claim 5.

8. A bacteria strain transformed with the nucleotide sequence of claim 5.

9. A bacteria strain comprising the expression vector of claim 7.

10. A method for preparing a carbonyl reductase mutant comprising an amino acid mutation;
    wherein the carbonyl reductase comprises the amino acid sequence of SEQ ID NO: 2, and the amino acid mutation comprises E101V, F214R or both E101V and F214R;
    the method comprising:
    constructing an expression vector according to claim 7, and transforming the expression vector into a recipient cell to generate a carbonyl reductase mutant transformant;
    culturing the carbonyl reductase mutant transformant in a culture medium and collecting the culture medium; and
    obtaining the carbonyl reductase mutant from the culture medium.

11. The method of claim 10, wherein the expression vector comprises a pET series expression vector.

12. The method of claim 11, wherein the pET series expression vector comprises a pET-28a expression vector.

13. A method for catalyzing a carbonyl reduction reaction, comprising:
    contacting a substrate with a carbonyl reductase mutant according to claim 1.

14. The method of claim 13, wherein the substrate comprises ethyl 6-oxo-8-chlorooctanoate.

15. A method for preparing ethyl (R)-6-hydroxy-8-chlorooctanoate, comprising:
    mixing a carbonyl reductase mutant according to claim 1 with a reaction solution containing ethyl 6-oxo-8-chlorooctanoate, and reacting to obtain ethyl (R)-6-hydroxyl-8-chlorooctanoate.

16. The method according to claim 15, wherein:
    the ethyl 6-oxo-8-chlorooctanoate has a mass percent concentration of 4% to 30%; the carbonyl reductase mutant is used in an amount of 5% to 30% by the weight of ethyl 6-oxo-8-chlorooctanoate;
    the reaction solution further comprises glucose dehydrogenase, a coenzyme and glucose; the glucose dehydrogenase in the reaction system is used in an amount of 3% to 10% by the weight of ethyl 6-oxo-8-chlorooctanoate;
    the coenzyme is NADP+;
    the coenzyme is used in an amount of $\frac{1}{10,000}$ to $\frac{5}{10,000}$ of the weight of ethyl 6-oxo-8-chlorooctanoate;
    the glucose is used in an amount 0.9-2 times the weight of ethyl 6-oxo-8-chlorooctanoate;
    the reaction is carried out in a solvent of Tris-HCl buffer, phosphate buffer, triethanolamine hydrochloride buffer, sodium acetate buffer or Tris-phosphate buffer; the reaction is carried out at pH 6.0 to 7.5;
    the reaction comprises a cosolvent comprising any one or a combination of at least two of ethanol, propanol, isopropanol, DMF, DMSO, polyethylene glycol or polysorbate 80;
    the cosolvent in the reaction is used in a volume percentage of 5% to 10% by the volume of the solvent;
    the reaction is carried out at a temperature of 20° C. to 35° C.; and
    the reaction is carried for a time of 4 to 24 hours.

17. A method for manufacturing (R)-α-lipoic acid, comprising the following steps:
    (1) preparing ethyl (R)-6-hydroxy-8-chlorooctanoate by using the carbonyl reductase mutant according to claim 12, and
    (2) preparing (R)-α-lipoic acid from the ethyl (R)-6-hydroxy-8-chlorooctanoate.

18. A method for manufacturing (R)-α-lipoic acid, comprising the following steps:
    (1) preparing ethyl (R)-6-hydroxy-8-chlorooctanoate by using the carbonyl reductase mutant transformant according to claim 8, and
    (2) preparing (R)-α-lipoic acid from the ethyl (R)-6-hydroxy-8-chlorooctanoate.

19. A method for manufacturing (R)-α-lipoic acid, including the following steps:
    (1) preparing ethyl (R)-6-hydroxy-8-chlorooctanoate via the method according to claim 14, and
    (2) preparing (R)-α-lipoic acid from the ethyl (R)-6-hydroxy-8-chlorooctanoate.

20. A method for manufacturing (R)-α-lipoic acid, including the following steps:
    (1) preparing ethyl (R)-6-hydroxy-8-chlorooctanoate via the method according to claim 15, and
    (2) preparing (R)-α-lipoic acid from the ethyl (R)-6-hydroxy-8-chlorooctanoate.

\* \* \* \* \*